(12) United States Patent
Park et al.

(10) Patent No.: US 11,864,799 B2
(45) Date of Patent: Jan. 9, 2024

(54) FAVORED ANGLE PEDICLE SCREW WITH ONE OR MORE OBLIQUE BORE SECTIONS FOR PREVENTING STRESS CONCENTRATIONS

(71) Applicant: Aesculap Inc., Center Valley, PA (US)

(72) Inventors: Jacob Park, Boyertown, PA (US); Jeffrey Tompkins, Quakertown, PA (US)

(73) Assignee: Aesculap Inc., Center Valley, PA (US)

( * ) Notice: Subject to any disclaimer, the term of this patent is extended or adjusted under 35 U.S.C. 154(b) by 68 days.

(21) Appl. No.: 17/562,076

(22) Filed: Dec. 27, 2021

(65) Prior Publication Data

US 2023/0200858 A1 Jun. 29, 2023

(51) Int. Cl.
*A61B 17/70* (2006.01)

(52) U.S. Cl.
CPC ...... *A61B 17/7032* (2013.01); *A61B 17/7038* (2013.01)

(58) Field of Classification Search
CPC ............ A61B 17/7032; A61B 17/7038; A61B 17/7034; A61B 17/7035; A61B 17/7037
See application file for complete search history.

(56) References Cited

U.S. PATENT DOCUMENTS

| | | | | |
|---|---|---|---|---|
| 5,891,145 A * | 4/1999 | Morrison | ............ | A61B 17/7037 606/267 |
| 6,974,460 B2 * | 12/2005 | Carbone | ............ | A61B 17/7082 606/305 |
| 8,137,386 B2 * | 3/2012 | Jackson | ............ | A61B 17/8863 606/266 |
| 8,137,387 B2 * | 3/2012 | Garamszegi | ....... | A61B 17/7037 606/270 |
| 9,277,942 B2 * | 3/2016 | Biedermann | ...... | A61B 17/7037 |
| 10,188,432 B2 * | 1/2019 | Jackson | ............ | A61B 17/7037 |
| 2003/0055426 A1 * | 3/2003 | Carbone | ............ | A61B 17/7037 606/305 |
| 2005/0154391 A1 * | 7/2005 | Doherty | ............. | A61B 17/7038 606/328 |
| 2005/0154393 A1 * | 7/2005 | Doherty | ............. | A61B 17/7037 606/267 |
| 2008/0132953 A1 * | 6/2008 | Carbone | ............ | A61B 17/7037 606/301 |
| 2009/0069852 A1 * | 3/2009 | Farris | ................. | A61B 17/7038 606/301 |

(Continued)

*Primary Examiner* — Ellen C Hammond
*Assistant Examiner* — Anna V. Little
(74) *Attorney, Agent, or Firm* — Christopher A. Rothe; Culhane Meadows PLLC (57) ABSTRACT

A favored angle screw assembly and a rod receiver body for a favored angle pedicle screw assembly. The favored angle screw assembly includes a pedicle screw and the rod receiver body. The rod receiver body includes a tubular wall having a first end with a first opening, a second end with a second opening, and a bore extending from the first opening to the second opening. The bore features a first bore section adjacent to the first opening, a second bore section adjacent the second opening, and a third bore section having a first end adjacent to the first bore section and a second end adjacent to the seat surface. The third bore section defines a transition surface that conforms to a side wall of an oblique three-dimensional shape.

23 Claims, 11 Drawing Sheets

Fig. 5A (56) References Cited

U.S. PATENT DOCUMENTS

| | | | |
|---|---|---|---|
| 2011/0087288 A1* | 4/2011 | Stevenson | A61B 17/7049 606/250 |
| 2012/0209336 A1* | 8/2012 | Jackson | A61B 17/7005 606/305 |
| 2012/0303063 A1* | 11/2012 | Cahill | A61B 17/7023 606/267 |
| 2013/0046350 A1* | 2/2013 | Jackson | A61B 17/7082 606/305 |
| 2013/0110178 A1* | 5/2013 | Biedermann | A61B 17/7038 606/305 |
| 2016/0354121 A1* | 12/2016 | Jackson | A61B 17/8685 |
| 2017/0333085 A1* | 11/2017 | Jackson | A61B 17/7038 |
| 2018/0110545 A1* | 4/2018 | Bush, Jr. | A61B 17/7032 |
| 2020/0121373 A1* | 4/2020 | Biedermann | A61B 17/8057 |
| 2021/0128202 A1* | 5/2021 | Jackson | A61B 17/8685 |

* cited by examiner

FIG. 1

(*Prior Art*)

FAVORED ANGLE PEDICLE SCREW WITH ONE OR MORE OBLIQUE BORE SECTIONS FOR PREVENTING STRESS CONCENTRATIONS

FIELD

The present disclosure relates generally to polyaxial bone screw assemblies and more particularly to a favored angle screw assembly with a rod receiver body that prevents stress concentrations from occurring in the wall of the rod receiver body.

BACKGROUND

Pedicle screws are used for stabilization of the spinal column in the case of fractures, tumors, infections, deformities and degenerative instabilities. A common practice is transpedicular screw fixation, in which pedicle screws are placed in the pedicles of adjacent vertebrae. A pedicle screw generally has an axial shaft or shank with a first end portion having an external thread and a second end portion with a so-called "tulip" or receiver body. The receiver body is a generally cylindrical structure with a longitudinal bore. The sidewall of the receiver body forms two U-shaped longitudinal slots that are diametrically opposed. The diametrically opposed slots form a transverse channel through the receiver body that intersects the bore. A longitudinal member or rod can be inserted transversely through the slots and fixed in each receiver body by a locking element, for example a grub screw or threaded nut, which engages threading in the receiver body.

There are two basic types of pedicle screws: monoaxial pedicle screws and polyaxial pedicle screws. In a monoaxial pedicle screw, the shaft and the receiver body are integrally formed with each other such that they are fixedly connected to each other. A polyaxial pedicle screw, in contrast, has a shaft and a separate receiver body. The shaft has an externally threaded portion at one end and a spherical or semi-spherical head at the opposite end. The receiver body typically has a hole at one end with a diameter larger than the diameter of the threaded portion but smaller than the diameter of the head. In this arrangement, the threaded portion projects out of the receiver body through the hole, while the head remains captive in the bore. The receiver body has a spherical or conical seat portion inside the hole that slidably engages the head. The slidable engagement between the head and seat portion allows the head and shank to pivot polyaxially relative to the receiver body.

Polyaxial pedicle screws can simplify lateral insertion of a rod through multiple receiver bodies after the pedicle screws are anchored in vertebrae. After each shaft is anchored into bone, each corresponding receiver body can be rotated and tilted until the U-shaped slots of all of the receiver bodies are sufficiently aligned to receive the rod. The hole in the rod receiver body allows each receiver body to tilt through an angular range about the head of the screw, and relative to the axis of the shaft. The maximum amount of tilting relative to the shaft axis in one direction is referred to herein as the "tilt angle" and the total range to which the receiver body can be pivoted relative to the shaft axis is referred to herein as "angulation".

Polyaxial pedicle screws typically have an axially symmetric design in which the receiver body has a uniform or constant tilt angle in all directions relative to the shaft axis. For example, a polyaxial pedicle screw may have a uniform tilt angle of 25° in all directions, thereby providing an angulation of 50°. The limits of this angulation can be characterized within a transverse plane as −25°/+25°.

In some instances, it is desirable to provide an asymmetric design in which the tilt angle is not constant in all directions, but rather, is larger in a specific direction relative to other directions. Polyaxial pedicle screws with these designs are referred to as "favored angle" pedicle screws due to their ability to provide more tilt angle in certain directions. Favored angle pedicle screws can have features in the receiver body that allow more tilt angle in certain directions. A common approach is to have a longitudinal bore through the receiver body with angularly offset bore sections. A first bore section is located at a proximal or "upper" section of the receiver body, and a second bore section is located at a distal or "lower" section of the receiver body. The first bore section has a first bore axis, and the second bore section has a second bore axis that is angularly offset from the first bore axis. The seat portion and/or hole at the lower or distal end of the receiver body is therefore tilted relative to the first bore axis. This tilting of the seat and/or hole allows the receiver body to tilt more in one direction than other directions. For example, a design can have a second bore axis offset from the first bore axis by 15°. A design with this offset has the same angulation of 50° as the previous example, but an angulation range of −10°/+40°.

One of the drawbacks of angularly offset bore sections is the tendency to have an abrupt transition or inside "corner" in the inner wall of the receiver body that surrounds some or all of the bore. For example, a 15° offset can create an abrupt ledge or corner where the first bore section intersects the second bore section. Abrupt ledges and corners are problematic because they create a stress concentration or stress riser in the receiver body when the screw head is seated and under load in-situ. When the locking element locks the rod into the receiver body, a significant amount of force is transferred to the receiver body wall. Such force can cause fatigue cracking or failure around the abrupt inside corner.

SUMMARY

The present disclosure provides a favored angle pedicle screw design that removes stress concentrations or risers without requiring larger receiver bodies or wall reinforcements.

In one beneficial aspect of the disclosure, a rod receiver body for a favored angle pedicle screw includes a tubular wall having a first end with a first opening, a second end with a second opening, and a bore extending from the first opening to the second opening. The bore can include a first bore section adjacent to the first opening, the first bore section defining a first bore axis, a second bore section adjacent the second opening, the second bore section defining a second bore axis and a seat surface that is symmetrical relative to the second bore axis, and a third bore section having a first end adjacent to the first bore section and a second end adjacent to the seat surface, the third bore section defining a transition surface that conforms to a side wall of an oblique three-dimensional shape.

In another beneficial aspect of the disclosure, the rod receiver body includes a transition surface that conforms to a frustum of an oblique cone.

In another beneficial aspect of the disclosure, the first end of the transition surface conforms to a base of an oblique cone.

In another beneficial aspect of the disclosure, the second end of the transition surface conforms to a plane through a midsection of an oblique cone.

In another beneficial aspect of the disclosure, a cross section of the bore taken through the first end of the transition surface defines a first ellipse having a first eccentricity, and a cross section of the bore taken through the second end of the transition surface defines a second ellipse having a second eccentricity less than the first eccentricity.

In another beneficial aspect of the disclosure, the third bore section defines a third bore axis extending from a center of the first ellipse to a center of the second ellipse.

In another beneficial aspect of the disclosure, the third bore axis is transverse to the first bore axis and transverse to the second bore axis.

In another beneficial aspect of the disclosure, the second eccentricity is zero, and the second ellipse is a circle.

In another beneficial aspect of the disclosure, an axial length of the second bore section measured along the second bore axis is longer than an axial length of the third bore section measured along the third bore axis.

In another beneficial aspect of the disclosure, the seat surface conforms to a sidewall of a right three-dimensional shape.

In another beneficial aspect of the disclosure, the seat surface conforms to a frustum of a right cone.

In another beneficial aspect of the disclosure, the seat surface has a proximal end adjacent to the second end of the transition surface, with the proximal end conforming to a base of a right cone.

In another beneficial aspect of the disclosure, the seat surface has a distal end adjacent to the second opening, the distal end conforming to a plane through a midsection of a right cone.

In another beneficial aspect of the disclosure, a favored angle pedicle screw assembly includes a pedicle screw having a screw head and a threaded shank. At least a portion of the screw head can feature a spherical surface. The favored angle pedicle screw assembly can also feature a rod receiver body with a tubular wall. The tubular wall can include a first end with a first opening, a second end with a second opening, and a bore extending from the first opening to the second opening. The bore can include a first bore section adjacent to the first opening, the first bore section defining a first bore axis, a second bore section adjacent the second opening, the second bore section defining a second bore axis and a seat surface that is symmetrical relative to the second bore axis, and a third bore section having a first end adjacent to the first bore section and a second end adjacent to the seat surface, the third bore section defining a transition surface that conforms to a side wall of an oblique three-dimensional shape. The pedicle screw can be securable in the rod receiver body in a seated position in which the spherical surface slidably engages the seat surface and does not contact the transition surface.

In another beneficial aspect of the disclosure, the transition surface conforms to a frustum of an oblique cone.

In another beneficial aspect of the disclosure, the first end of the transition surface conforms to a base of an oblique cone.

In another beneficial aspect of the disclosure, the second end of the transition surface conforms to a plane through a midsection of an oblique cone.

In another beneficial aspect of the disclosure, a cross section of the bore taken through the first end of the transition surface defines a first ellipse having a first eccentricity, and a cross section of the bore taken through the second end of the transition surface defines a second ellipse having a second eccentricity less than the first eccentricity.

In another beneficial aspect of the disclosure, the third bore section defines a third bore axis extending from a center of the first ellipse to a center of the second ellipse.

In another beneficial aspect of the disclosure, the second eccentricity is zero, and the second ellipse is a circle.

BRIEF DESCRIPTION OF THE DRAWINGS

The foregoing summary and the following detailed description will be better understood in conjunction with non-limiting examples shown in the drawing figures, of which.

DETAILED DESCRIPTION

Figure 1:
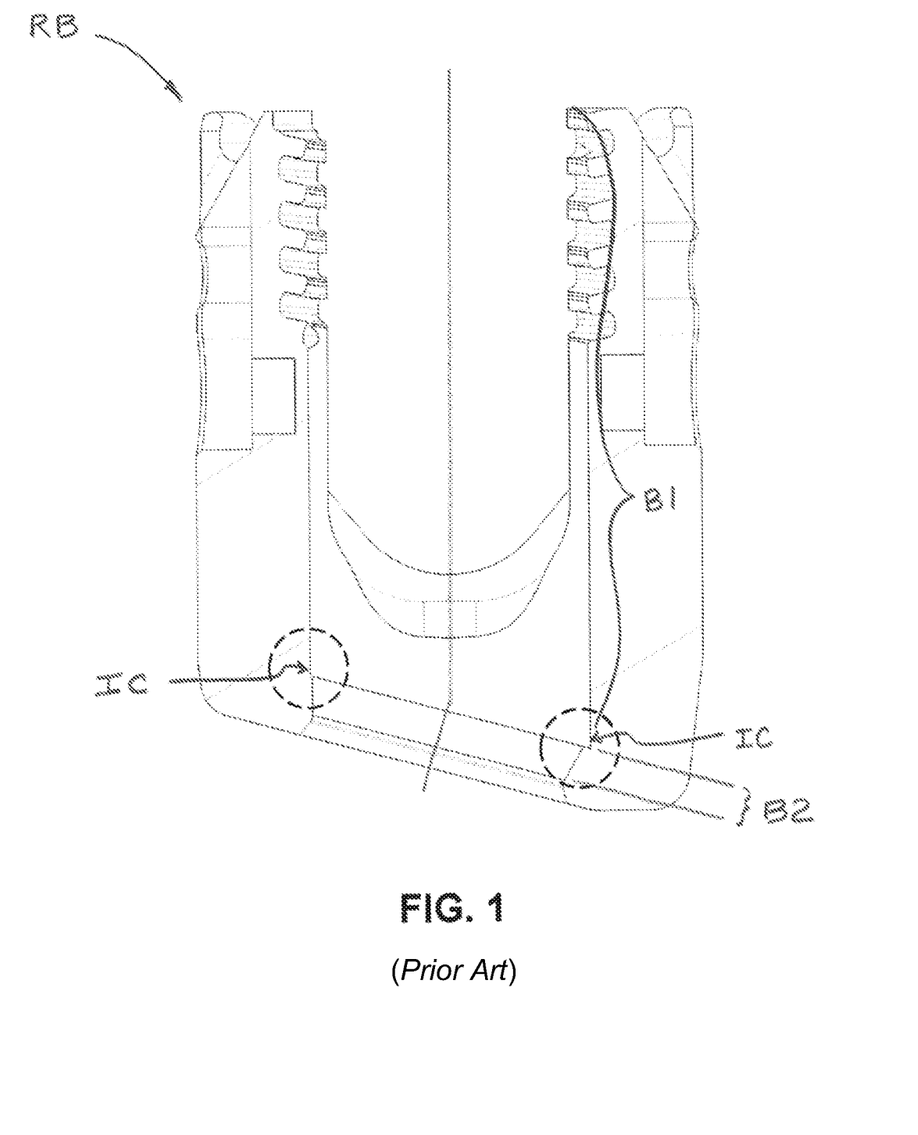
FIG. 1 is a cross sectional view of a conceptual receiver body design for a favored angle pedicle screw having a bore design that is susceptible to stress concentrations.
Figure 2:
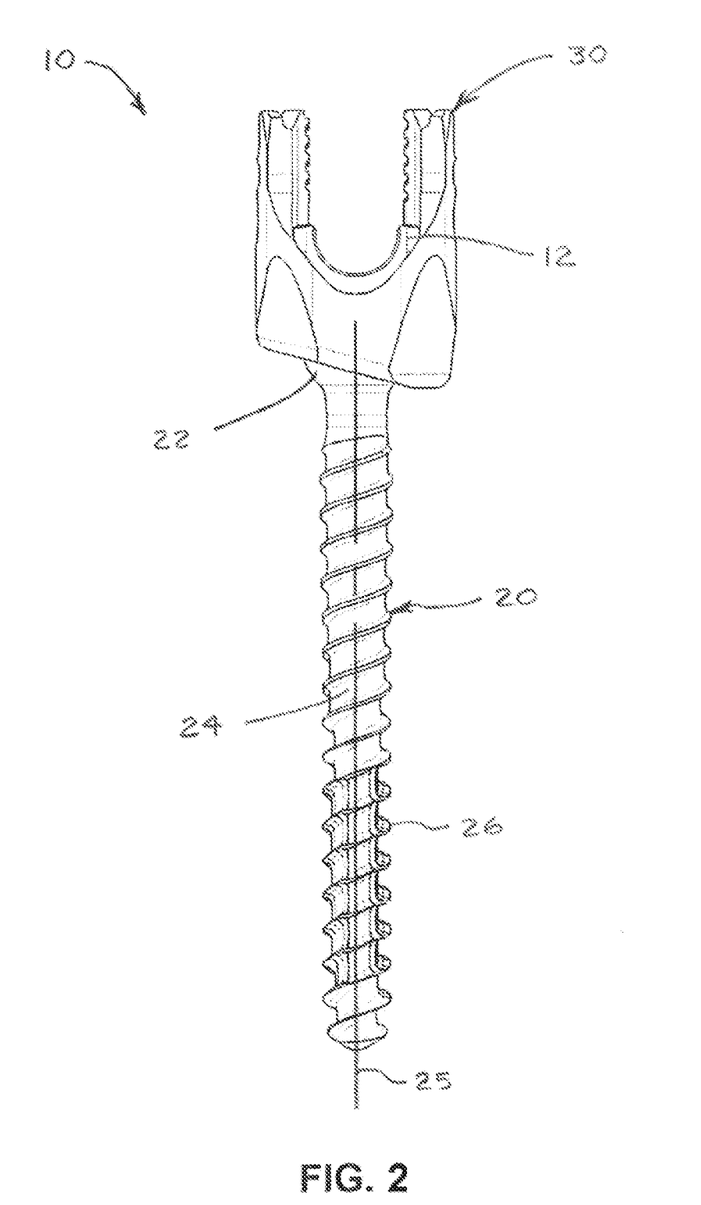
FIG. 2 is a front view of a favored angle pedicle screw according to one embodiment of the present disclosure.
Figure 3:
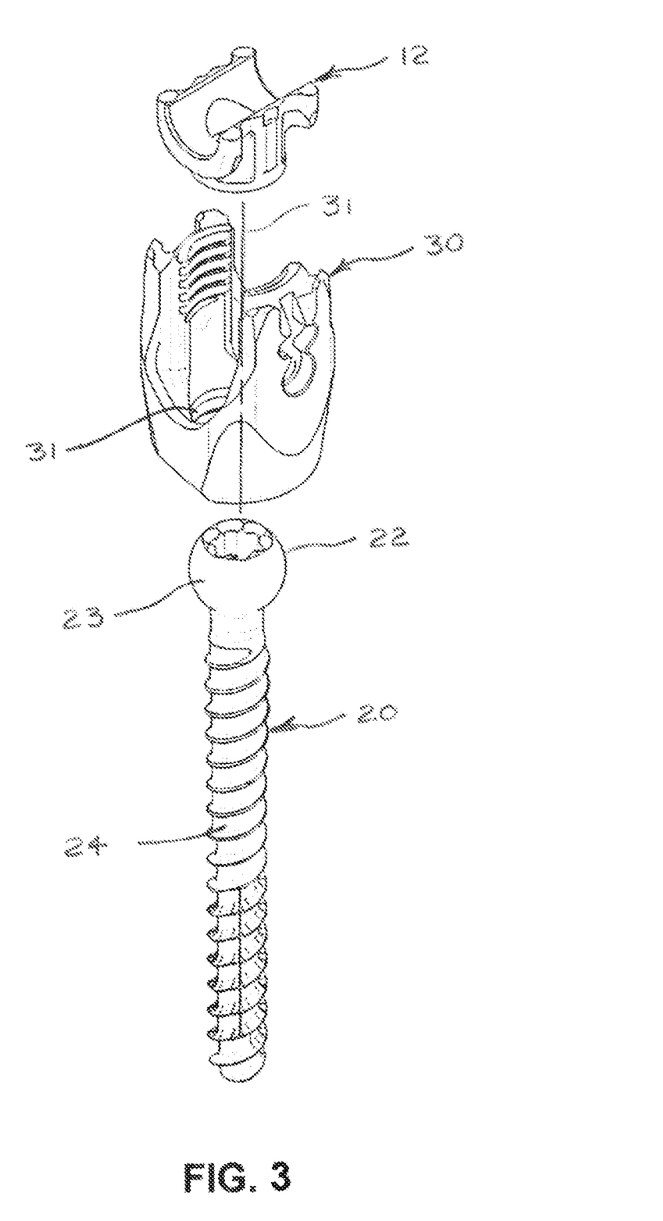
FIG. 3 is an exploded perspective view of the favored angle pedicle screw of FIG. 2.

Referring to FIG. 1, a conceptual design of a favored angle receiver body RB is shown that is susceptible to stress concentrations. Receiver body RB has a first bore section B1 and a second bore section B2 that is directly adjacent to and angularly offset from first bore section B1. First bore section B1 is generally cylindrical, while second bore section B2 has a cone shaped geometry configured to seat the head of bone screw. The angular offset and change in direction creates an abrupt edge or inside corner IC where the first bore section intersects the second bore section. Inside corner IC is circled in two diametrically opposed locations in FIG. 1. Abrupt inside corners like inside corner IC are problematic because they create a stress concentration or stress riser in the receiver body when the screw head is seated and under load in-situ. When the locking element locks the rod into the receiver body, a significant amount of force is transferred to the receiver body wall. Such force can cause fatigue cracking or failure around the abrupt inside corner Referring to FIGS. 2 and 3, a favored angle pedicle screw assembly 10 ("assembly") is shown according to one embodiment of the present disclosure. Assembly 10 has a bone screw 20 and a receiver body 30 into which the bone screw 20 is received. An insert 12 is inserted in receiver body 30 to support a longitudinal member or rod and transfer compression force from a locking element to bone screw 20. Bone screw 20 has a head portion 22 and an elongated shank portion 24 attached to the head portion. In addition, bone screw 20 defines a screw axis 25 that extends through the longitudinal center of head portion 22 and shank portion 24. Head portion 22 has a spherical surface 23 designed to be seated on a seat surface 31 inside receiver body 30. Spherical surface 23 bears against and slidably engages seat surface 31 in an unlocked state. Shank portion 24 has an external thread 26 configured to be driven into bone and is cannulated to enable assembly 10 to pass over a guidewire. Receiver body 30 is designed to pivot or tilt in a polyaxial range of motion relative to screw axis 25 after shank portion 24 is anchored in bone.

Assembly 10 is designed to provide receiver body 30 with an asymmetrical range of motion relative to screw axis 25. The phrase "asymmetrical range of motion" as used herein means that the receiver body has more tilt angle in certain directions as compared to other directions relative to screw axis 25. As such, bone screw 20 can pivot more in certain directions relative to a longitudinal axis 37 of receiver body 30 than in other directions.

Figure 4:
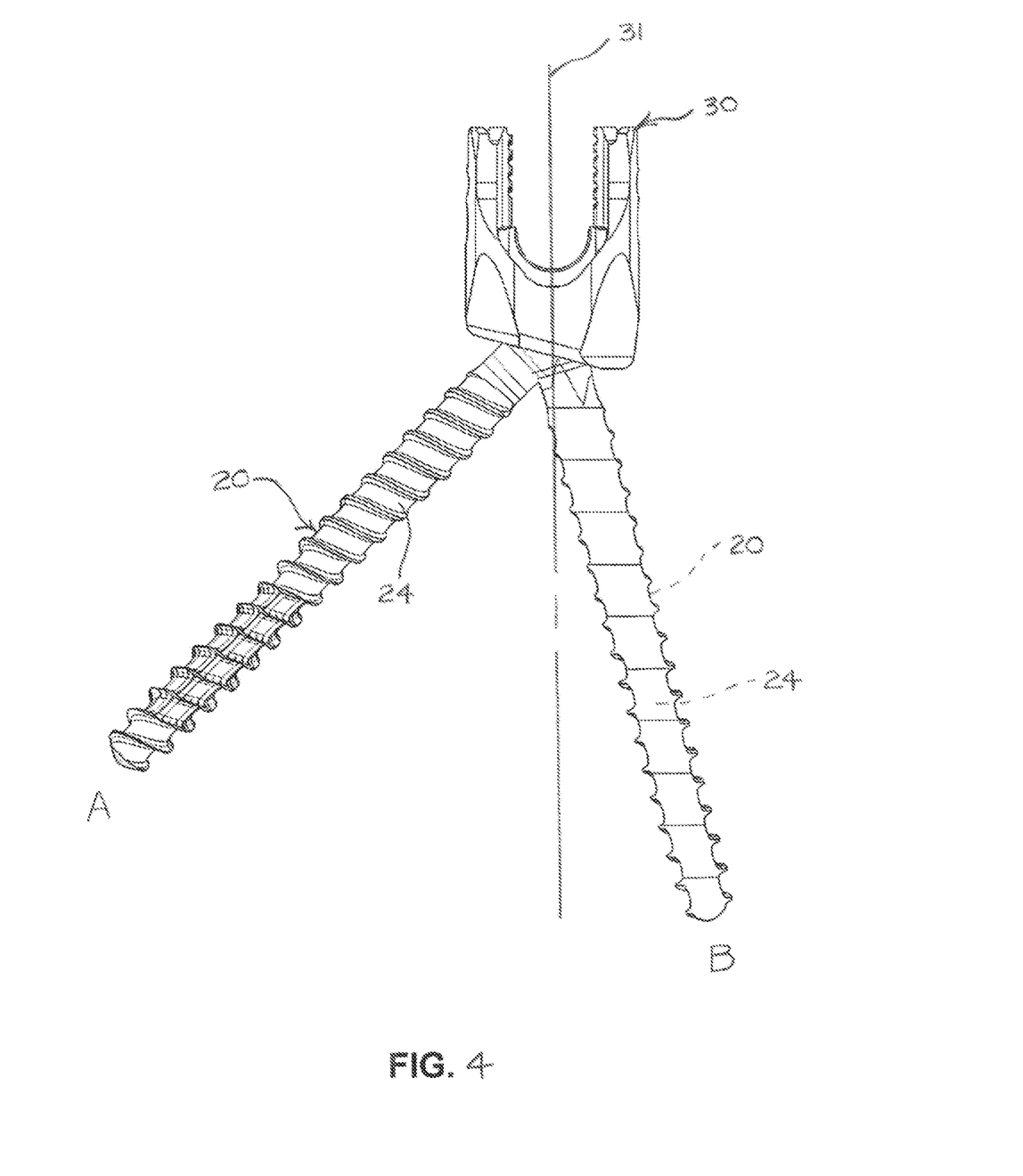
FIG. 4 is another front view of the favored angle pedicle screw of FIG. 2 showing a bone screw in two possible orientations.

The asymmetrical range of motion of bone screw 20 (and hence receiver body 30) is illustrated in FIG. 4, which shows how the bone screw can assume two different positions A and B relative to the receiver body. Shank portion 24 is in the same vertical plane in positions A and B, and positions A and B represent maximum tilt angles in opposite directions. In position A, bone screw 20 is pivoted −40° relative to longitudinal axis 37 of receiver body 30. In position B, bone screw 20 is pivoted +10° relative to longitudinal axis 37 of receiver body 30.

Figure 5:
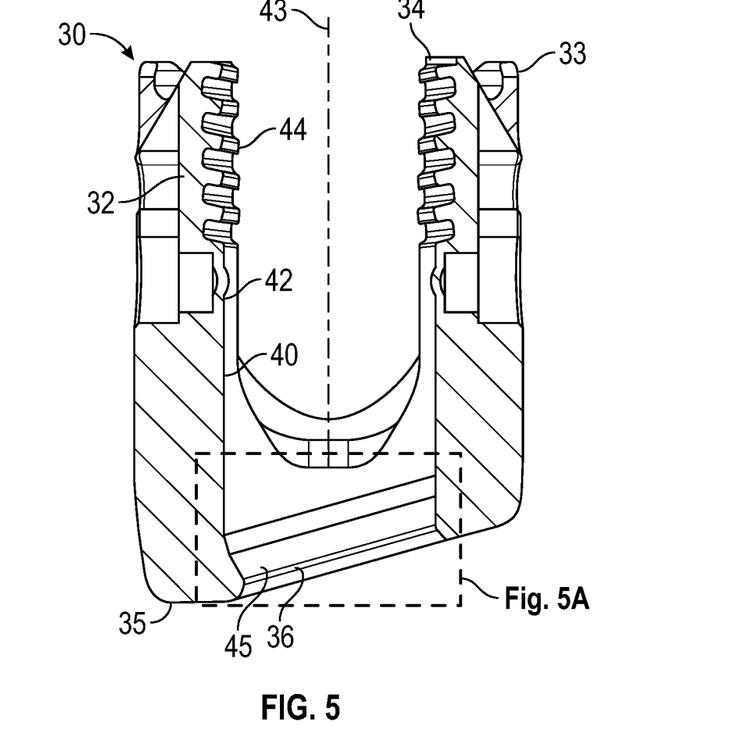
FIG. 5 is a cross sectional view of a receiver body of the favored angle pedicle screw of FIG. 2.
Figure 5A:
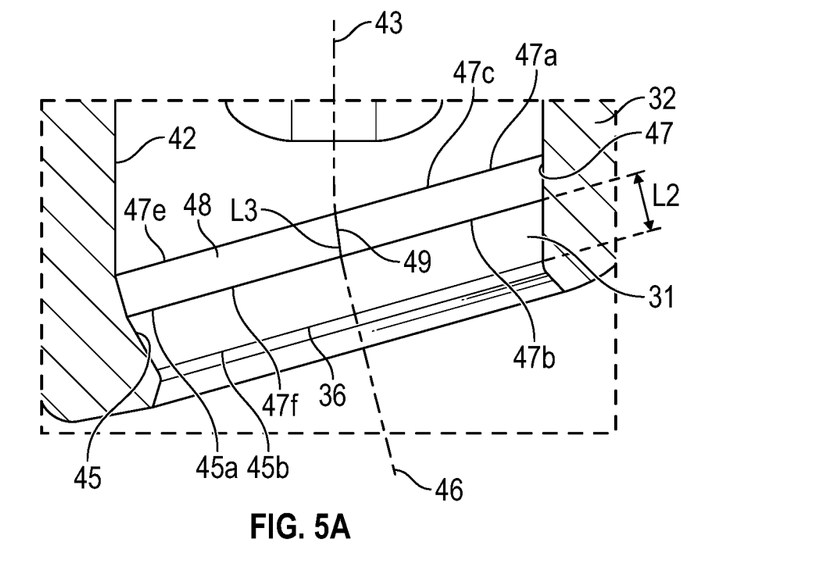
FIG. 5A is an enlarged view of one area of the receiver body shown in FIG. 5.
Figure 6:
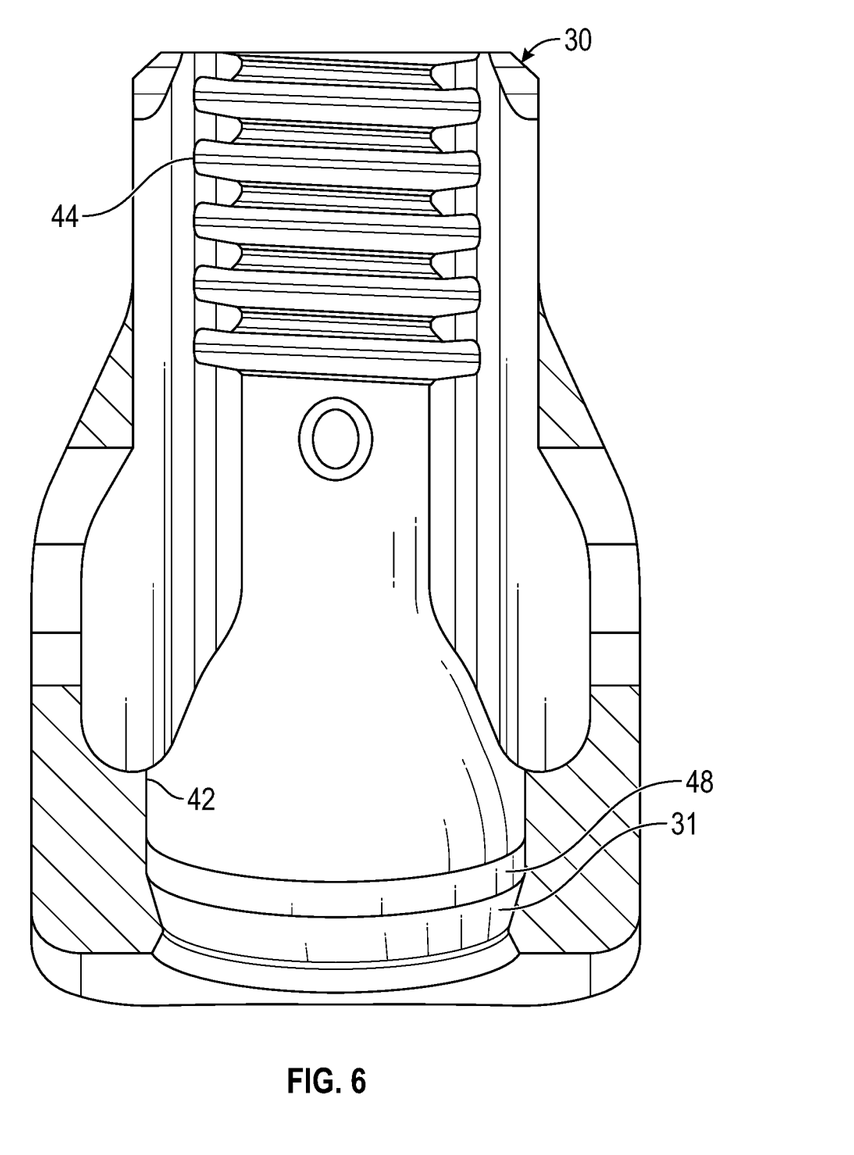
FIG. 6 is another cross sectional view of the receiver body shown in FIG. 5.

Referring to FIGS. 5, 5A and 6, receiver body 30 defines a tubular wall 32 having a first end 33 with a first opening 34, a second end 35 with a second opening 36, and a bore 40 extending from the first opening to the second opening. Bore 40 has a first bore section 42 adjacent to the first opening 34 and a second bore section 45 adjacent second opening 36.

Each bore section according to the present disclosure has a bore axis. The term "bore axis" as used herein refers to an axis that extends between the center point of one end of the bore section to the center point of the opposite end of the bore section, as will be shown in the accompanying drawing figures. Referring to FIG. 5A, first bore section 42 defines a first bore axis 43 and an internal thread 44. Second bore section 45 defines a second bore axis 46 and forms seat surface 31. Seat surface 31 is symmetrical relative to second bore axis 46, as will be explained.

To prevent the occurrence of stress concentrations in tubular wall 32, bore 40 has a third bore section 47 that forms a transition surface 48 between first bore section 42 and second bore section 45. Transition surface 48 is contoured to eliminate what would otherwise be an abrupt discontinuity in tubular wall 32 if first bore section 42 were otherwise located directly adjacent to second bore section 45. Third bore section 47 has a first end 47a adjacent to first bore section 42, a second end 47b adjacent to seat surface 31, and a third bore axis 49 extending between the first and second ends as shown in FIG. 5A.

Transition surfaces and seat surfaces according to the present disclosure can have a variety of wall geometries that function together to facilitate a favored tilting direction while avoiding edges that create stress concentrations. For example, the wall geometries can be rounded, flat, or a combination of rounded and flat. Any combination of shapes can be selected to the first, second and third bore sections that eliminates jagged or abrupt edges between bore sections. Cone shaped surfaces have an advantage of being very easy to machine compared to other geometries. In addition, cone surfaces reduce stress risers and potentially damaging outside corners or edges. Moreover, cone shaped seat surfaces reduce the potential for the screw to adhere or stick to the seat surface, such as during unlocking.

Transition surfaces and seat surfaces according to the present disclosure can have geometries that conform to a sections taken through a variety of three dimensional shapes. For example, the wall geometries can conform to frustums. The term "frustum" as used herein means the portion of a cone or pyramid that remains after an upper part comprising the vertex is cut off by a plane parallel to the base, or a portion that remains between two cutting planes that are parallel to the base. Wall geometries can also conform to truncated shapes. The term "truncated shape" as used herein means the portion of a cone or pyramid that remains after an upper part comprising the vertex is cut off by a plane non-parallel to the base, or a portion that remains between two cutting planes that are non-parallel to each other.

Wall geometries can conform to frustums or other three-dimensional shapes that are symmetrical or asymmetrical. Examples of symmetrical geometries include a frustum of a right cone or a frustum of a right pyramid. The term "right" as used herein refers to a three-dimensional shape having a base and a vertex, wherein a line connecting the center point of the base to the vertex is perpendicular to the plane of the base. Thus, the term "right" can apply to certain cones and pyramids. In the case of a right cone, the base can be circular (a circular cone) or elliptical (an elliptical cone). In the case of a right pyramid, the base can have any number of sides, such as three sides (triangular pyramid), four sides (square pyramid), or more sides. In the case of other right three-dimensional shapes, the bottom face can have a first shape and the top face can have a second shape different from the first shape.

Examples of asymmetrical geometries include a frustum of an oblique cone, a frustum of an oblique pyramid, a truncated oblique cone, a truncated oblique pyramid, or other oblique three-dimensional shape. The term "oblique" as used herein refers to a three-dimensional shape having either a base and a vertex (e.g. cone or pyramid) or a flat bottom face and a flat top face, wherein a line connecting the center point of the base/bottom face to the vertex/center of top face is non-perpendicular to the plane of the base/bottom face. Thus, the term "oblique" can apply to certain cones and pyramids. In the case of an oblique cone, the base can be circular (oblique circular cone) or elliptical (oblique elliptical cone). In the case of an oblique pyramid, the base can have any number of sides, such as three sides (oblique triangular pyramid), four sides (oblique square pyramid), or more sides. In the case of other oblique three-dimensional shapes, the bottom face can have a first shape, such as an oval or ellipse, and the top face can have a second shape, such as a circle, that is different from the first shape.

FIGS. 7-16 illustrate non-limiting examples of symmetrical and asymmetrical geometries of seat surfaces and transition surfaces according to the present disclosure. These geometries include frustums, truncated three-dimensional shapes, and other types of three-dimensional shapes, any of which can define the shapes of seat surfaces and transition surfaces according the present disclosure.

Figure 7:
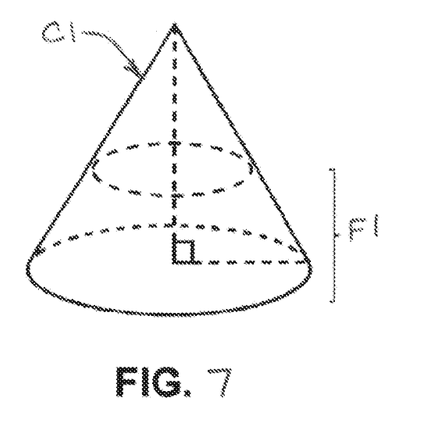
FIGS. 7-16 illustrate different geometries that can be used for seat surfaces and transition surfaces according to the present disclosure.
Figure 8:
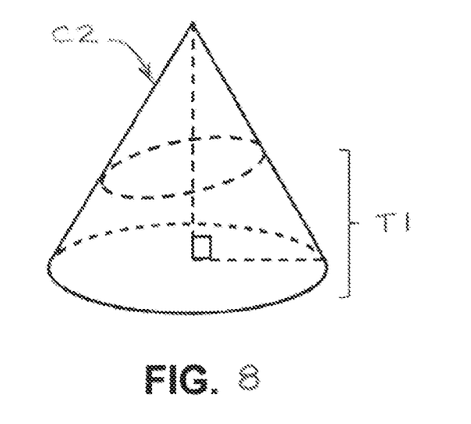
Figure 9:
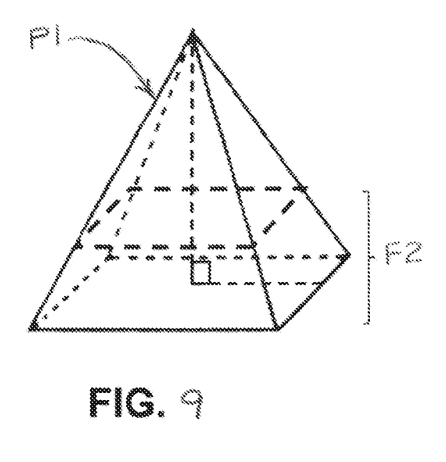
Figure 10:
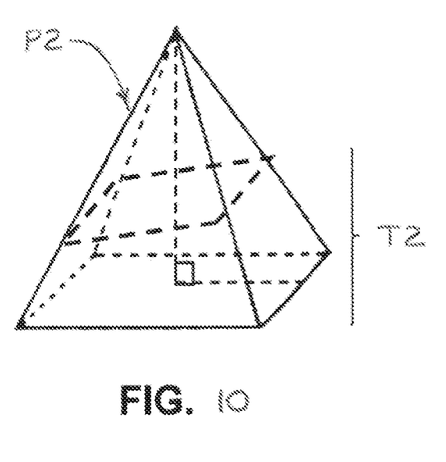
Figure 11:
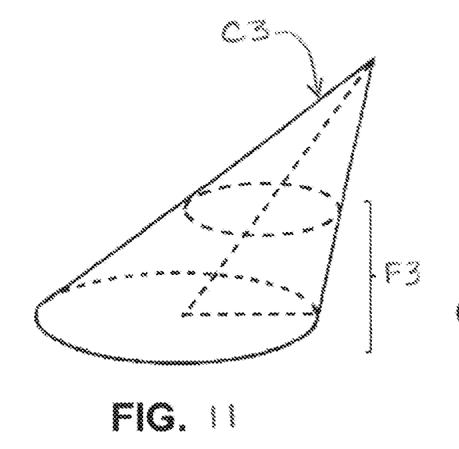
Figure 12:
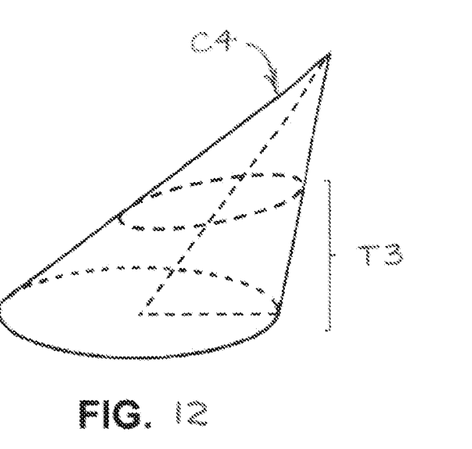
Figure 13:
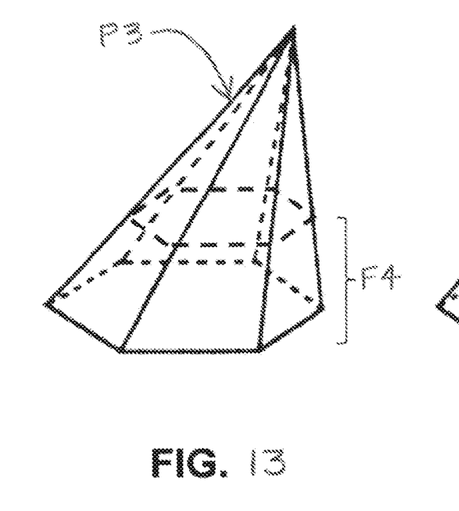
Figure 14:
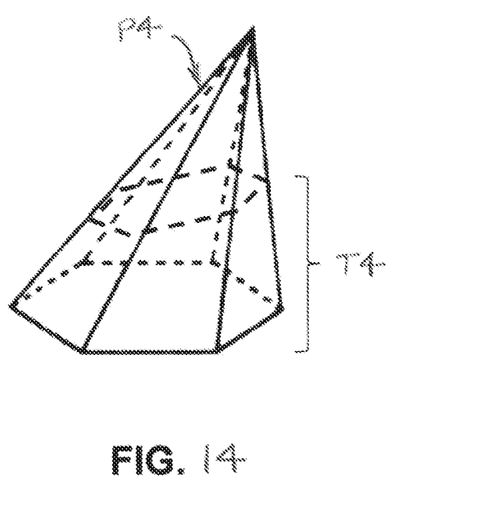
Figure 15:
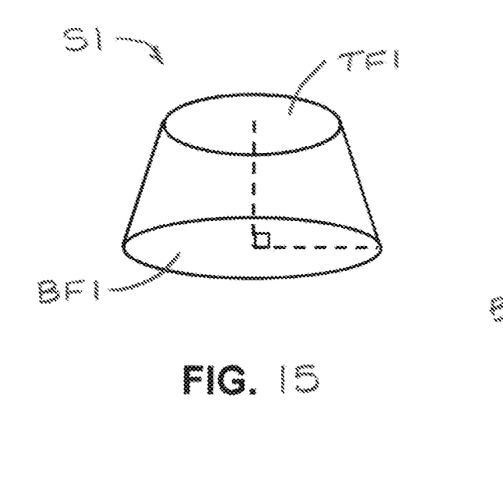
Figure 16:
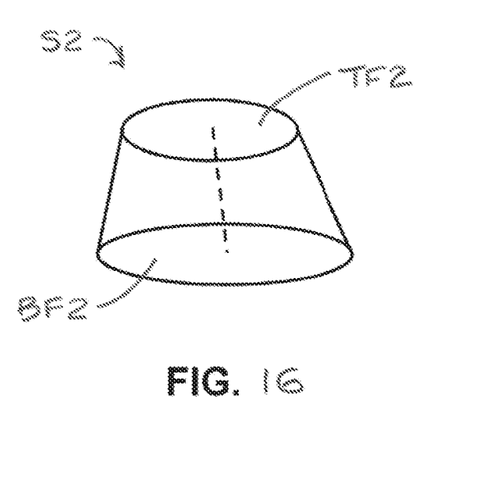

FIG. 7 shows an example of a right cone C1 with a frustum F1, and FIG. 8 shows an example of a right cone C2 with a truncated right cone portion T1. FIG. 9 shows an example of a right square pyramid P1 and a frustum F2, and FIG. 10 shows an example of a right square pyramid P2 with a truncated right square pyramid portion T2. FIG. 11 shows an example of an oblique cone C3 with a frustum F3, and FIG. 12 shows an example of an oblique cone C4 with a truncated oblique cone portion T3. FIG. 13 shows an oblique hexagonal pyramid P3 with a frustum F4, and FIG. 14 shows an oblique hexagonal pyramid P4 with a truncated oblique hexagonal pyramid portion T4. Finally, FIGS. 15 and 16 show examples of other three-dimensional shapes. FIG. 15 shows an example of a right three-dimensional shape S1 having an elliptical bottom face BF1 and a circular top face TF1, and FIG. 16 shows an example of an oblique three-dimensional shape S2 having an elliptical bottom face BF2 and a circular top face TF2.

In the frustum examples shown in FIGS. 7, 9, 11 and 13, the top surfaces of the frustums are parallel to the bases. In the truncated examples shown in FIGS. 8, 10, 12 and 14, the top surfaces of the truncated portions are transverse or non-parallel to the bases. In the examples shown in FIGS. 15 and 16, the circular top faces are parallel to the elliptical bottom faces. It will be understood, however, that the top faces and bottom faces in FIGS. 15 and 16 could also be non-parallel, providing further examples of other three-dimensional shapes that can be used to shape bore sections according to the present disclosure. In all of the foregoing examples, the smaller top surfaces or top faces correspond to the smaller end of a bore section, and the larger bases or bottom faces correspond to the larger end of the bore section.

Figure 17:
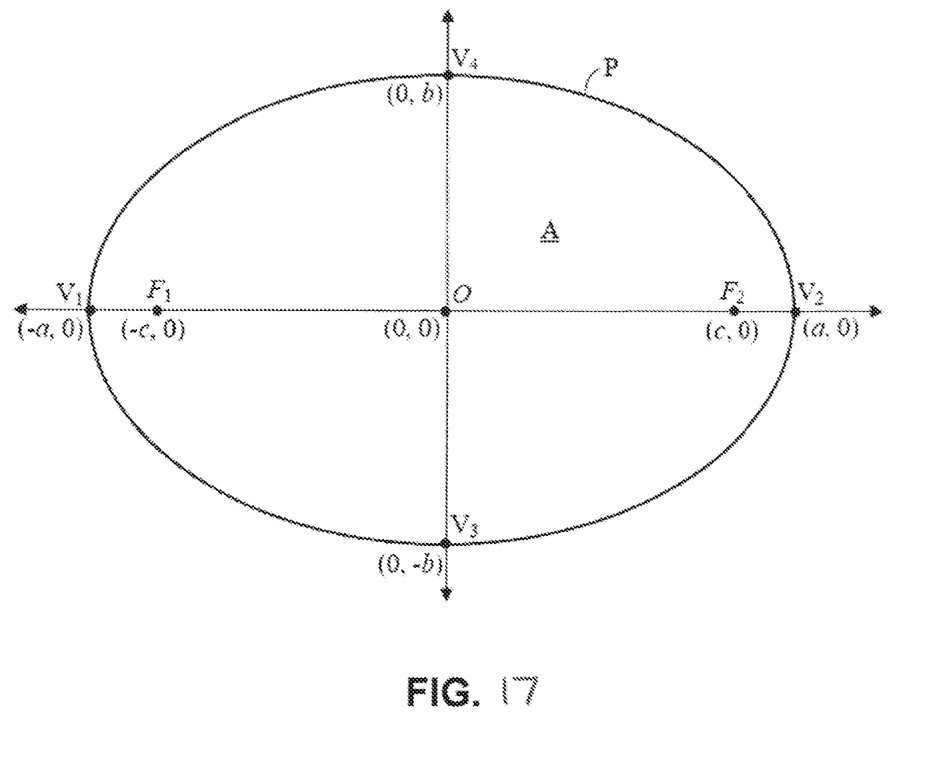
FIG. 17 is a cross section view of a bore section of the receiver body of FIG. 5 with its geometry represented with Cartesian coordinates.

FIG. 17 shows one example of an elliptical bore cross section according to the present disclosure that can be present in a transition surface, a seat surface, or both. The cross section is shown with various points represented as Cartesian coordinates. The center of the bore cross section is the origin O of the ellipse. The major axis of the ellipse extends between a first vertex $V_1$ at (−a, 0) and a second vertex $V_2$ at (a, 0). The minor axis of the ellipse extends between a third vertex $V_3$ at (0, −b) and a fourth vertex $V_4$ at (0, b). The first focus $F_1$ is at (−c, 0) and the second focus $F_2$ is at (c, 0). The ratio c/a is referred to as the eccentricity e of the ellipse. P represents the perimeter of the ellipse, and A represents the cross sectional area of the ellipse.

Elliptical bore sections can conform to elliptical cones, in which all cross sections conform to an ellipse. All of the elliptical cross sections can have the same eccentricity e. It has been discovered, however, that elliptical cross sections with gradually changing eccentricities provide desirable results, particularly with transition surfaces. One reason for this is that a gradual decrease in eccentricity allows the cross-sectional shape of the transition surface to change from an ellipse where it intersects the first bore section to a more circular shape or a circle where it intersects the second bore section. This smooth transition facilitates the change in angle between the first and second bore sections without creating abrupt inside corners that create stress risers.

Referring back to FIG. 5A, seat surface 31 is symmetrical with respect to second bore axis 46. Second bore section 45 has a first end 45a with a cross section conforming to a circle with a first diameter, and a second end 45b with a cross section conforming to a circle with a second diameter less than the first diameter. First end 45a corresponds to a base of a circular cone, and second end 45b corresponds to a plane through a midsection of the circular cone. Second bore axis 46 intersects a plane through first end 45a perpendicularly. As such, seat surface 31 has a wall geometry that conforms to a frustum of a right cone. The conic geometry of seat surface 31 and rounded geometry of spherical surface 23 on head portion 22 create a slidable engagement in which a very small surface area of the head portion contacts the seat surface at any one time when the head portion is seated.

Figure 18:
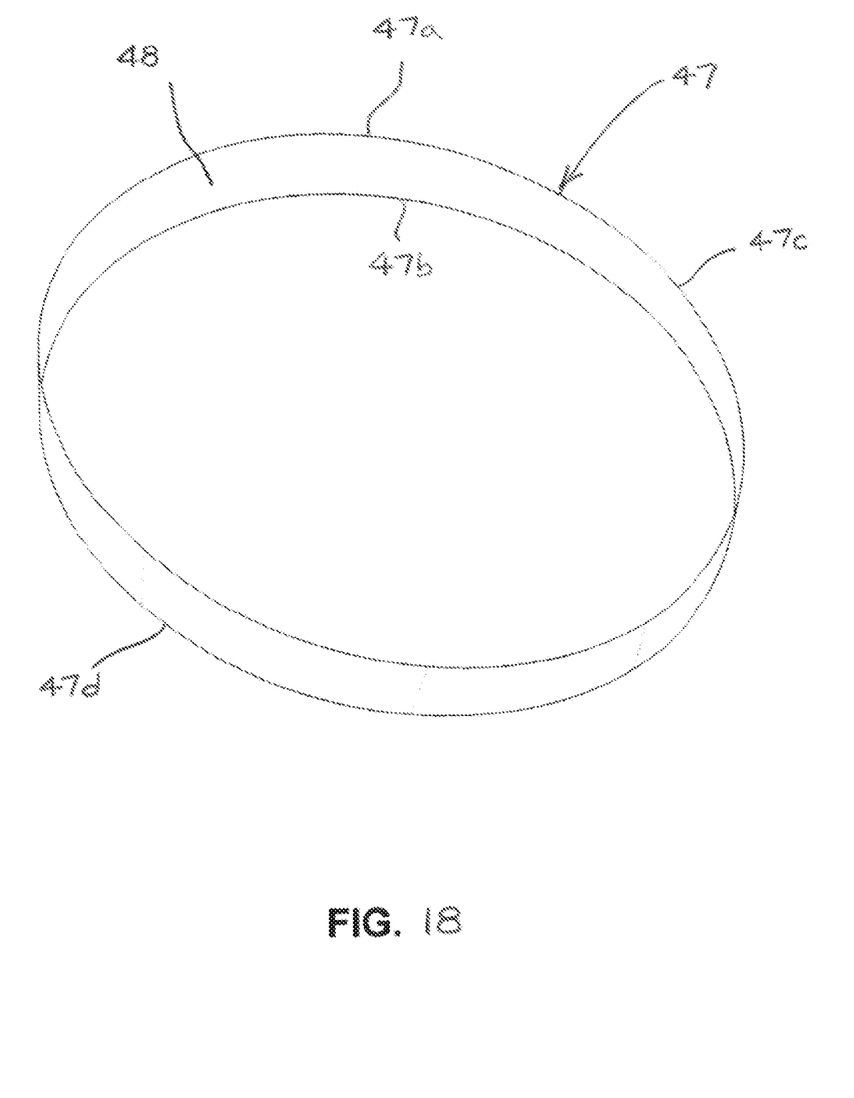
FIG. 18 is a three-dimensional outline of the bore section of FIG. 15.

Unlike seat surface 31, transition surface 48 has an asymmetrical wall geometry. First end 47a of third bore section 47 has a cross section conforming to a first ellipse 47c with a first eccentricity $e_1$ that is greater than zero. Second end 47b of third bore section 47 has a cross section conforming to a second ellipse 47d with a second eccentricity $e_2$ that is less than the first eccentricity $e_1$. In particular, second eccentricity $e_2$ is zero. Therefore, second ellipse 47d is a circle and merges seamlessly with first end 45a of second bore section 45, which is also circular. Third bore axis 49 connects the center point of the first ellipse at first end 47a and the center point of the circle at second end 47b. First ellipse 47c extends within a first end plane 47e, and second ellipse 47d extends within a second end plane 47f that is parallel to first end plane 47e. The eccentricity e of each cross section decreases uniformly, or in a linear manner, as the third bore section extends from first end 47a to second end 47b. Therefore, transition surface 48 conforms to a three-dimensional shape with an elliptical cross section at a first end and a circular cross section at a second end. This geometry corresponds to the oblique three-dimensional shape S2 shown in FIG. 16. A schematic line drawing of transition surface 48 is shown in FIG. 18.

The elliptical cross section of a transition surface according to the present disclosure can decrease from a maximum eccentricity at the first end to a minimum eccentricity, such as zero, at the second end. The maximum eccentricity can be in the range of about 0.2 to about 0.3. Elliptical cross sections with lower or higher eccentricities can also be used. In the present example, the elliptical cross section at first end 47a is defined by the values shown in the Table below, with points represented as Cartesian Coordinates and dimensions measured in mm:

TABLE

| (CROSS SECTION OF FIRST END IN TRANSITION SECTION) | |
|---|---|
| Origin (O) | (0, 0) |
| First Focus ($F_1$) | (−0.9913, 0) |
| Second Focus ($F_2$) | (0.9913, 0) |
| First Vertex ($V_1$) | (−3.8305, 0) |
| Second Vertex ($V_2$) | (3.8305, 0) |
| Third Vertex ($V_3$) | (0, −3.7) |
| Fourth Vertex ($V_4$) | (0, 3.7) |
| Eccentricity ($e_1$) | 0.2588 |
| Area | 44.525 mm$^2$ |
| Perimeter | 23.66 mm |

Referring again to FIG. 5A, third bore axis 49 extends transversely to first bore axis 43 and transversely to second bore axis 46. First bore axis 43 and second bore axis 46 intersect at a point inside third bore section 47. An axial length L2 of second bore section 45 measured along second bore axis 46 is longer than an axial length L3 of third bore section 47 measured along third bore axis 49. It will be understood that axial lengths L2 of second bore sections according to the present disclosure can also be less than or equal to axial lengths L3 of third bore sections. A shorter axial length L3 of the third bore section may be desirable, however, insofar as it occupies less space within the bore and allows the other bore sections to occupy a larger fraction of the body. Third bore section 47 represents a very small fraction of the total bore length through receiver body 30.

Figure 19:
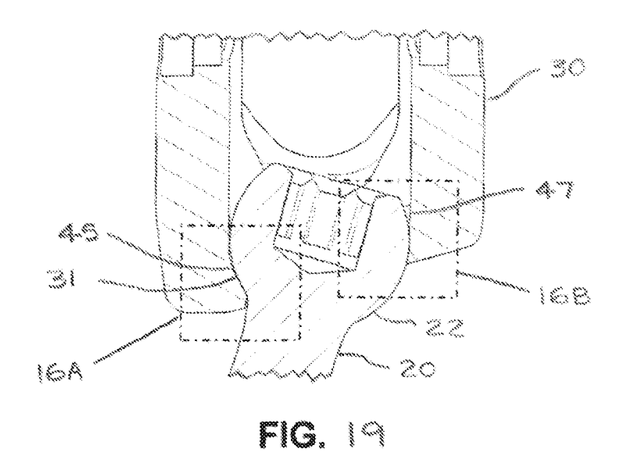
FIG. 19 is a truncated cross-sectional view of the favored angle pedicle screw of FIG. 1 showing the engagement between the screw head and receiver body.
Figure 19A:
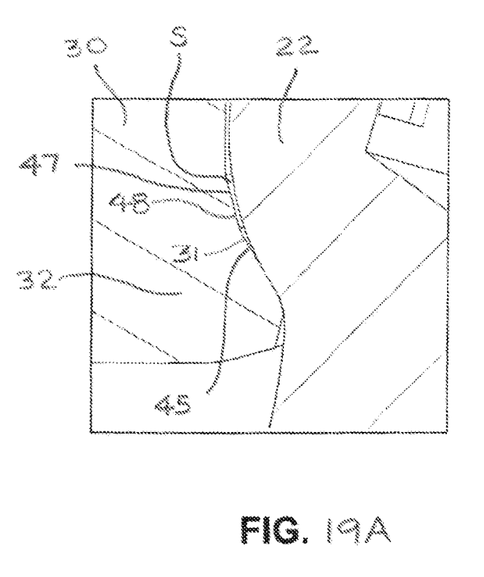
FIG. 19A is an enlarged cross-sectional view of a first area of the favored angle pedicle screw shown in FIG. 19.
Figure 19B:
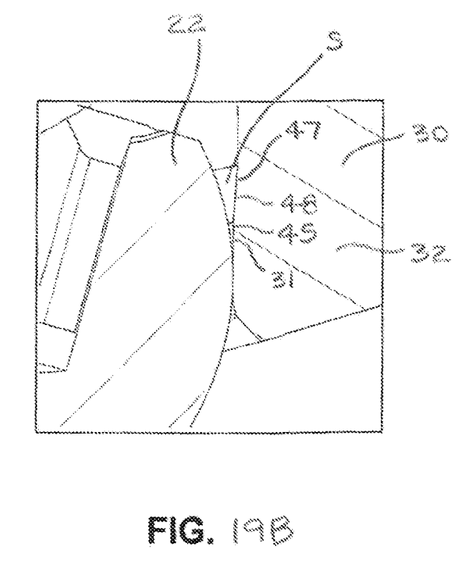
FIG. 19B is an enlarged cross-sectional view of a second area of the favored angle pedicle screw shown in FIG. 19.

Referring now to FIGS. 19, 19A and 19B, bone screw 20 is shown inside receiver body 30, with head portion 22 of the bone screw seated on seat surface 31. Second bore section 45 and third bore section 47 are arranged in a configuration that prevents any contact between head portion 22 and transition surface 48 when the bone screw is seated. Head portion 22 is configured to slidably engage seat surface 31 through a polyaxial range of motion when seated while avoiding contact with transition surface 48. Third bore section 47 provides a clearance space S between head portion 22 and tubular wall 32 when the head portion is seated in any orientation within the polyaxial range of motion. Clearance space S is more visible in FIGS. 19A and 19B, which provide magnified views of the seated head portion 22 in FIG. 16. In this arrangement, head portion 22 only contacts seat surface 31 and does not contact transition surface 48. Clearance space S is present around the entire circumference of head portion 22 when bone screw 20 is seated, regardless of the bone screw's orientation relative to receiver body 30.

Although this description makes reference to specific embodiments and illustrations, the claims are not intended to be limited to the details shown. For example, the seat surface need not conform to a frustum of a right cone. In addition, the transition surface need not be made up of elliptical cross sections with an eccentricity e that decreases as the transition surface extends from the first end to the second end. The seat surface and/or transition surface can conform to other geometries, including but not limited to those shown in FIGS. 7-16.

For example, other designs according to the present disclosure can feature a seat surface conforming to a right or oblique three-dimensional shape, including but not limited to the frustum of a right or oblique pyramid, a truncated right or oblique cone, or a truncated right or oblique pyramid. In addition, other designs according to the present disclosure can feature a transition surface conforming to a right or oblique three-dimensional shape, including but not limited to the frustum of a right or oblique pyramid, a truncated right or oblique cone, or a truncated right or oblique pyramid.

Transition surfaces according to the present disclosure can also have elliptical cross sections with other degrees of eccentricity than those described. For example, the eccentricity of the elliptical cross section at the second end of the third bore section can be slightly greater than zero, so as to provide a near-circular shape. In addition, the eccentricity of cross sections along the third bore section need not decrease in a linear manner toward the second end, and can instead have a non-linear change in eccentricity, with sidewalls following a curvature or other non-conical geometry.

Any combination of geometries can be selected, including but not limited to combinations with one or more oblique bore sections, or one or more elliptical cross sections. Accordingly, the present disclosure encompasses various modifications and combinations of the specific embodiments and illustrations described herein, including variations that may be made within the scope and range of equivalents of the originally filed claims.

What is claimed:

1. A rod receiver body for a favored angle pedicle screw, the rod receiver body comprising:
a tubular wall having a first end with a first opening, a second end with a second opening, and a bore extending from the first opening to the second opening, the bore comprising:
a first bore section adjacent to the first opening, the first bore section defining a first bore axis;
a second bore section adjacent the second opening, the second bore section defining a second bore axis and a seat surface that is symmetrical relative to the second bore axis; and
a third bore section having a first end immediately adjacent to and continuous with the first bore section and a second end immediately adjacent to and continuous with the seat surface, the third bore section defining a transition surface that conforms to a side wall of an oblique three-dimensional shape.

2. The rod receiver body according to claim 1, wherein the transition surface conforms to a frustum of an oblique cone.

3. The rod receiver body according to claim 2, wherein the first end of the transition surface conforms to a base end of the oblique cone, wherein the oblique cone has a maximum cross-sectional area at the base end.

4. The rod receiver body according to claim 3, wherein the second end of the transition surface conforms to a plane through a midsection of the oblique cone.

5. The rod receiver body according to claim 1, wherein a cross section of the bore taken through the first end of the transition surface defines a first ellipse having a first eccentricity, and a cross section of the bore taken through the second end of the transition surface defines a second ellipse having a second eccentricity less than the first eccentricity.

6. The rod receiver body according to claim 5, wherein the third bore section defines a third bore axis extending from a center of the first ellipse to a center of the second ellipse.

7. The rod receiver body according to claim 6, wherein the third bore axis is transverse to the first bore axis and transverse to the second bore axis.

8. The rod receiver body according to claim 6, wherein the second eccentricity is zero, and the second ellipse is a circle.

9. The rod receiver body according to claim 6, wherein an axial length of the second bore section measured along the second bore axis is longer than an axial length of the third bore section measured along the third bore axis.

10. The rod receiver body according to claim 1, wherein the seat surface conforms to a sidewall of a right three-dimensional shape.

11. The rod receiver body according to claim 10, wherein the seat surface conforms to a frustum of a right cone.

12. The rod receiver body according to claim 11, wherein the seat surface has a proximal end adjacent to the second end of the transition surface, said proximal end conforming to a base of the right cone.

13. The rod receiver body according to claim 12, wherein the seat surface has a distal end adjacent to the second opening, the distal end conforming to a plane through a midsection of the right cone.

14. A favored angle pedicle screw assembly comprising:
A. a pedicle screw having a screw head and a threaded shank, at least a portion of the screw head comprising a spherical surface; and
B. a rod receiver body comprising a tubular wall having a first end with a first opening, a second end with a second opening, and a bore extending from the first opening to the second opening,
the bore comprising:
i. a first bore section adjacent to the first opening, the first bore section defining a first bore axis;
ii. a second bore section adjacent the second opening, the second bore section defining a second bore axis and a seat surface that is symmetrical relative to the second bore axis; and iii. a third bore section having a first end immediately adjacent to and continuous with the first bore section and a second end immediately adjacent to and continuous with the seat surface, the third bore section defining a transition surface that conforms to a side wall of an oblique three-dimensional shape, the pedicle screw being securable in the rod receiver body in a seated position in which the spherical surface slidably engages the seat surface and does not contact the transition surface.

15. The favored angle pedicle screw assembly according to claim 14, wherein the transition surface conforms to a frustum of an oblique cone.

16. The favored angle pedicle screw assembly according to claim 15, wherein the first end of the transition surface conforms to a base end of the oblique cone, wherein the oblique cone has a maximum cross-sectional area at the base end.

17. The favored angle pedicle screw assembly according to claim 16, wherein the second end of the transition surface conforms to a plane through a midsection of the oblique cone.

18. The favored angle pedicle screw assembly according to claim 15, wherein a cross section of the bore taken through the first end of the transition surface defines a first ellipse having a first eccentricity, and a cross section of the bore taken through the second end of the transition surface defines a second ellipse having a second eccentricity less than the first eccentricity.

19. The favored angle pedicle screw assembly according to claim 18, wherein the third bore section defines a third bore axis extending from a center of the first ellipse to a center of the second ellipse.

20. The favored angle pedicle screw assembly according to claim 18, wherein the second eccentricity is zero, and the second ellipse is a circle.

21. A rod receiver body for a favored angle pedicle screw, the rod receiver body comprising:

a tubular wall having a first end with a first opening, a second end with a second opening, and a bore extending from the first opening to the second opening, the bore comprising:

a first bore section adjacent to the first opening, the first bore section defining a first bore axis;

a second bore section adjacent the second opening, the second bore section defining a second bore axis and a seat surface that is symmetrical relative to the second bore axis; and a third bore section having a first end defining a first end plane immediately adjacent to and continuous with the first bore section and a second end defining a second end plane immediately adjacent to and continuous with the seat surface, the third bore section defining a transition surface that conforms to a side wall of an oblique three-dimensional shape.

22. The rod receiver body according to claim 21, wherein the first end plane of the transition surface conforms to a base end of the oblique cone, wherein the oblique cone has a maximum cross-sectional area at the base end.

23. The rod receiver body according to claim 22, wherein the second end plane of the transition surface conforms to a plane through a midsection of the oblique cone.

\* \* \* \* \*